(12) United States Patent  (10) Patent No.: US 8,808,352 B2
Eells et al.  (45) Date of Patent: Aug. 19, 2014

(54) CAST BIOREMODELABLE GRAFT

(75) Inventors: Scott E. Eells, Bloomington, IN (US);
Michael C. Hiles, Lafayette, IN (US);
Thomas A. Osborne, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 412 days.

(21) Appl. No.: 11/054,043

(22) Filed: Feb. 9, 2005

(65) Prior Publication Data
US 2005/0187604 A1 Aug. 25, 2005

Related U.S. Application Data

(60) Provisional application No. 60/542,922, filed on Feb. 9, 2004.

(51) Int. Cl.
*A61F 2/06* (2013.01)
(52) U.S. Cl.
USPC .......................................................... 623/1.13
(58) Field of Classification Search
USPC .............. 623/1.13, 2.38, 2.42, 1.16
See application file for complete search history.

(56) References Cited

U.S. PATENT DOCUMENTS

| | | | | |
|---|---|---|---|---|
| 5,968,096 | A * | 10/1999 | Whitson et al. | 424/423 |
| 6,187,036 | B1 * | 2/2001 | Shaolian et al. | 623/1.15 |
| 6,254,632 | B1 * | 7/2001 | Wu et al. | 623/1.15 |
| 6,379,710 | B1 * | 4/2002 | Badylak | 424/553 |
| 7,163,563 | B2 * | 1/2007 | Schwartz et al. | 623/14.12 |
| 2004/0044395 | A1 * | 3/2004 | Nelson | 623/1.12 |
| 2005/0113905 | A1 * | 5/2005 | Greenberg et al. | 623/1.16 |
| 2005/0171594 | A1 * | 8/2005 | Machan et al. | 623/1.13 |
| 2005/0222668 | A1 * | 10/2005 | Schaeffer et al. | 623/1.13 |
| 2007/0031508 | A1 * | 2/2007 | Armstrong et al. | 424/572 |

* cited by examiner

*Primary Examiner* — Tuan V Nguyen
(74) *Attorney, Agent, or Firm* — Brinks Gilson & Lione

(57) ABSTRACT

A cast bioremodelable graft (22) including a cast tubular construct (33) of a bioremodelable substance (34). The bioremodelable substance is cast on or applied to a form and then vacuum pressed to dry or harden the substance. Expandable members (18) are disposed on, in, under or about the cast tubular construct to expand the graft when released from an endoluminal delivery system. A second layer (39) can be applied over the first layer (38) and the expandable stents to contain the stents there between without the need for any separate attachment. The graft is dehydrated and preferably vacuum pressed to harden the bioremodelable substance. The form is removed to form one or more lumens (23-25) in the graft, which is then loaded on an endoluminal delivery system.

17 Claims, 6 Drawing Sheets

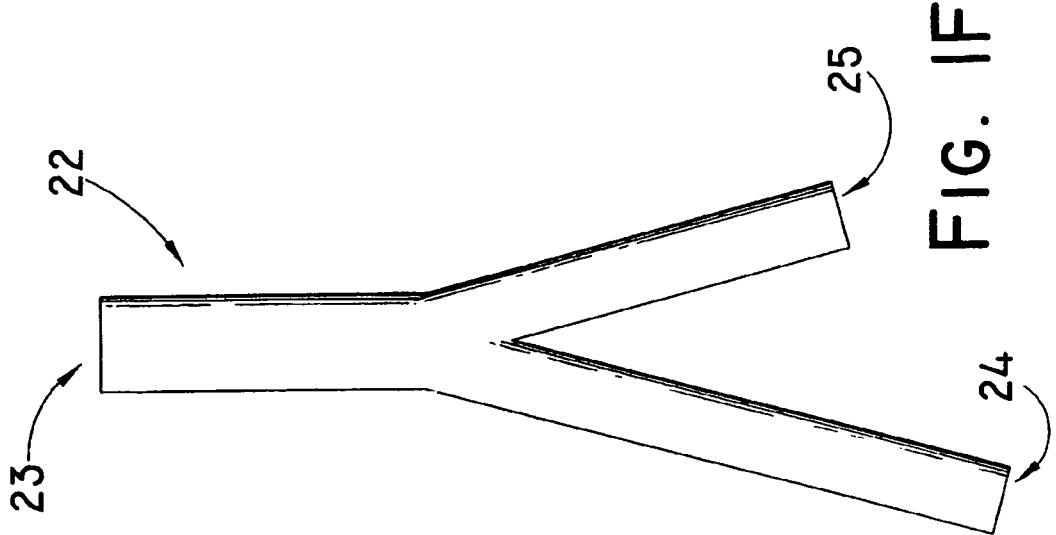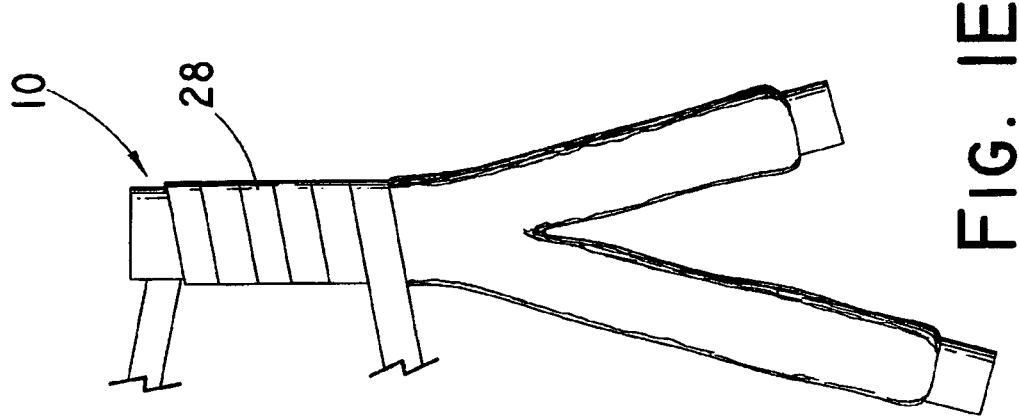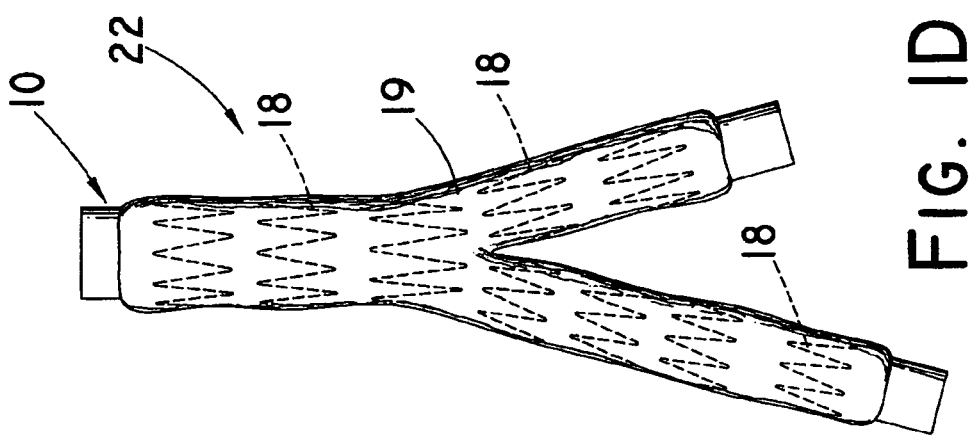

CAST BIOREMODELABLE GRAFT

CROSS-REFERENCE TO RELATED APPLICATIONS

This application claims priority of provisional application Ser. No. 60/542,922, filed Feb. 9, 2004.

TECHNICAL FIELD

This invention relates generally to medical devices and, in particular, to surgical graft, stent grafts, stent graft materials, and methods for making surgical grafts and stent grafts. These grafts and stent grafts are primarily used for abdominal aortic aneurysm grafting and stent grafting, but can be used in other areas of the vasculature for stent grafting, aneurysm exclusion, bypass, etc.

BACKGROUND OF THE INVENTION

Vasculature graft materials are generally of two main types, woven Dacron textile and expanded polytetrafluoroethylene (ePTFE). Both of these materials are synthetic materials and only marginally tolerated by the body. In the case of stent grafts, they are subject to wear because they are assembled to metallic spring expansion members, commonly known as stents, which cause wear of the graft material at attachment points. In addition, these synthetic grafts are relatively thick and when they are collapsed for introduction into the body through introducer sheaths, they require very large sheaths, making percutaneous introduction very difficult.

SUMMARY OF THE INVENTION

The foregoing problems are solved and a technical advance is achieved in an illustrative embodiment of a cast bioremodelable graft of the present invention. This graft advantageously comprises a cast tubular construct of a bioremodelable substance such as preferably an extracellular collagen matrix material that causes tissue or cells coming in approximate contact therewith to remodel.

The graft material of this invention is preferably a bioremodelable substance that includes, amongst others, at least one of growth factors, a resorbable material, an extracellular collagen matrix material, a synthetic material, and a binder material. Preferably the bioremodelable substance is an extracellular collagen matrix material and, in particular, small intestine submucosal (SIS) tissue, collagen or other natural material that has, for example, growth factors to induce tissue remodeling. SIS in its normal sheet form has widely varying differences in its thickness and porosity on any given piece of material. Instead of using the SIS material in its normally occurring sheet form, the SIS can be cut into pieces or can be shredded or ground into small sized bits or particles. These small pieces or bits can then be uniformly sprayed, formed or cast on to a mandrel of the appropriate shape and size for the desired graft. The malleable, hydrated pieces are cast on or applied like papier mache to a form. After the cast is dried or allowed to harden, the form is removed, and a cast tubular construct results. The SIS particles can be sprayed or, preferably cast onto the mandrel with or without a binder material to enhance the physical strength of the resulting structure. An expandable member such as Z stents of the appropriate size and strength can be embedded in the SIS material as it is being formed on the mandrel. The resulting SIS with embedded stents is then subjected to pressure as in vacuum bagging, tape wrapping or other suitable method so as to compress the SIS particles close together during curing and binding thus producing a material with uniform thickness and porosity. In addition, since the expandable members or preferably Z stents are fully incorporated into the wall structure of the graft, no suturing would be required to hold the stents to the graft material. The elimination of the suture material greatly reduces the collapsed profile of the stent graft, making it more suited to percutaneous placement and reduces the possibility of wear on the graft material by eliminating areas of movement or "rubbing" between the stent struts and graft material.

This invention is directed to a graft material that is accepted by the body and eventually remodeled into natural tissue and that incorporates the expanding frame members into its construction so as to significantly reduce the profile or collapsed size for percutaneous introduction.

In another embodiment, the SIS material can be ground or shred into fine, fibrous particles or strands which would then be spun into a fine yarn or thread. This thread can then be woven into the desired graft form in a manner similar to existing woven Dacron grafts. A thin nitinol wire or other resilient material can be woven into the warf and/or weft at certain intervals to give the graft "body" or the ability to expand and maintain its shape without additional stents being attached to the graft.

The bioremodelable substance can be naturally occurring or synthetic with growth factors to cause the remodeling of tissue or cells coming in approximate contact therewith. Preferably, the bioremodelable substance also includes a resorbable material and can also include a binder material for interconnecting pieces or particles of the bioremodelable material. In a more preferred embodiment of the cast bioremodelable expandable graft, the graft also includes an expandable member disposed preferably in the bioremodelable substance to eliminate the need for any further attachment to the cast tubular construct. In addition, a second layer of the bioremodelable substance can be applied to the first layer with the expandable member disposed between the two layers. Preferably, the bioremodelable substance includes pieces or particles of extracellular collagen matrix material such as SIS which can be then vacuum pressed to advantageously obtain a thinner wall thickness or profile. Any binder material is preferably a resorbable material and preferably comprises, amongst others, at least one of a biodegradable polymer, a collagen, a fibrin, a fibronectin, and a polysaccharide.

BRIEF DESCRIPTION OF THE DRAWINGS

FIG. 1D depicts the first layer construct and expandable member Z stents thereon of FIG. 1C with a second layer of a bioremodelable substance cast on or applied over the first layer and expandable member Z stents;

FIG. 1E depicts the tubular construct of FIG. 1D, with a wrap of polytetrafluoroethylene or other polymer wrap wound around the construct to compress the SIS pieces or particles and Z stents for curing or drying;

FIG. 1F depicts an illustrative embodiment of the completed stent graft of the present invention of FIG. 1D after compression curing or vacuum pressing of the bioremodelable substance and removal of the form or mandrel from the tubular construct and trimming the ends thereof;

DETAILED DESCRIPTION

Figure 1:
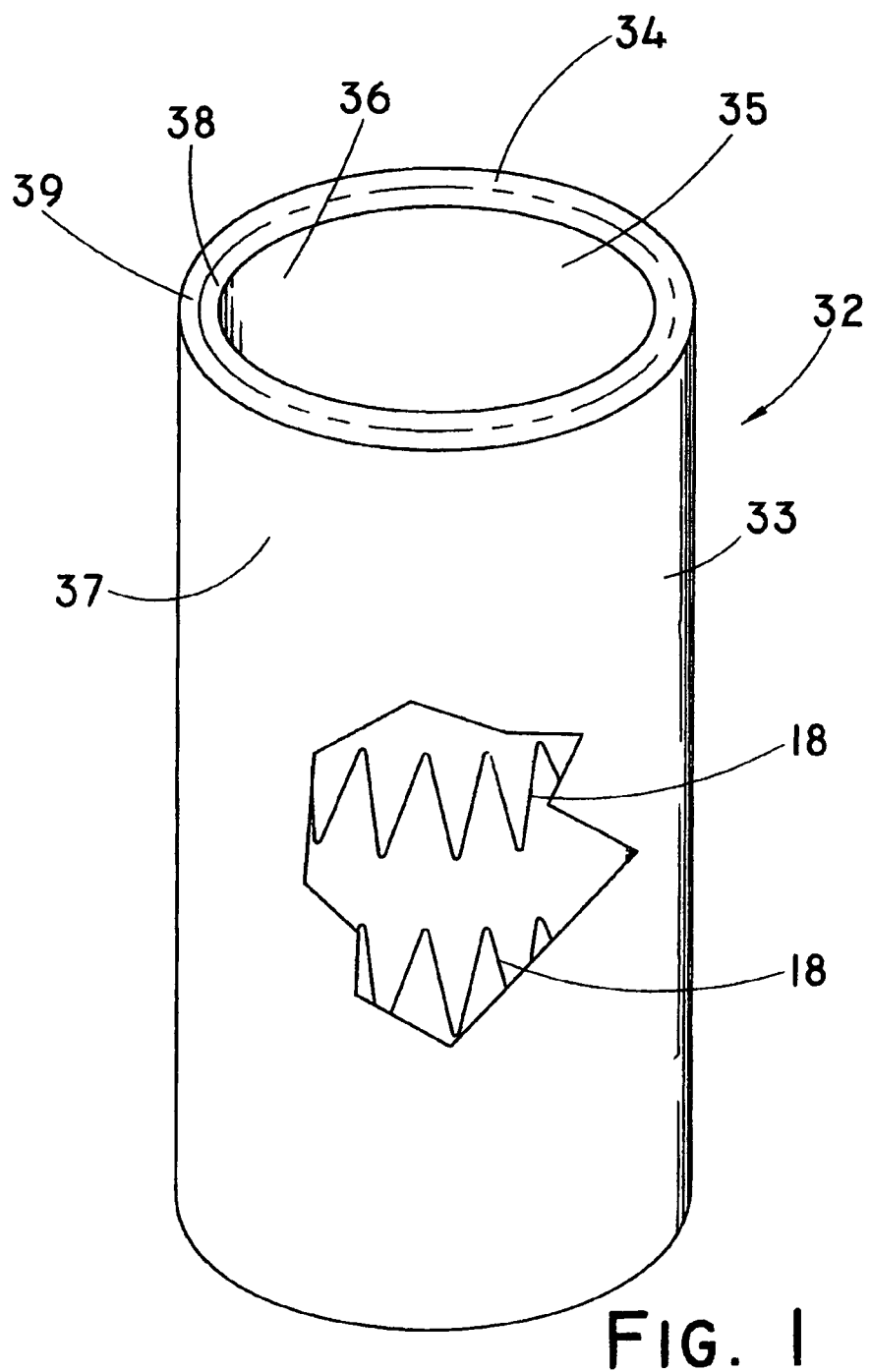
FIG. 1 depicts a pictorial view of an illustrative cast bioremodelable graft of the present invention with expandable members disposed in the cast tubular construct of a bioremodelable substance.

FIG. 1 depicts a pictorial view of an illustrative cast bioremodelable graft 32 of the present invention with optional expandable members 18 such as Z stents disposed in the cast tubular construct 33 of a bioremodelable substance 34. The tubular construct has a lumen 35 extending longitudinally there through with inside surface 36 and outside surface 37. The tubular construct 33 also includes a first layer 38 of the bioremodelable substance and optionally a second layer 39 of the bioremodelable substance disposed on the first layer with the expandable member such as stent 18 there between. Although the expandable member 18 expands the cast graft between a compressed state and expanded state and are preferably utilized in an endoluminal embodiment when positioned in a minimally invasive delivery system. The cast graft can also be utilized in an endovasculature or other duct system in an open surgical procedure in which the graft is sutured or stapled to the ends of the vessel or duct. The bioremodelable substance is any biocompatible substance that includes typically growth factors or other proteins and the like for inducing tissue or cells coming in contact therewith to remodel.

Figure 1C:
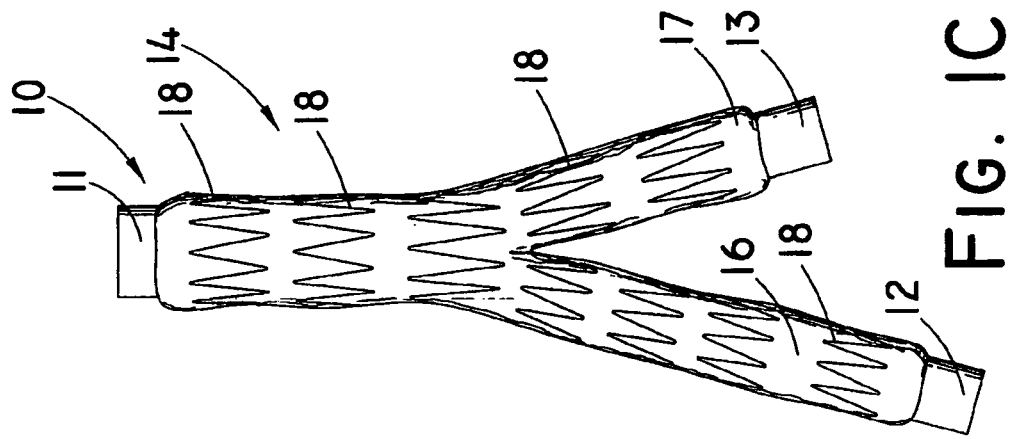
FIG. 1C depicts the first layer of the bioremodelable substance cast on or applied to the mandrel of FIG. 1B with the expandable member Z stents disposed thereon.
Figure 1B:
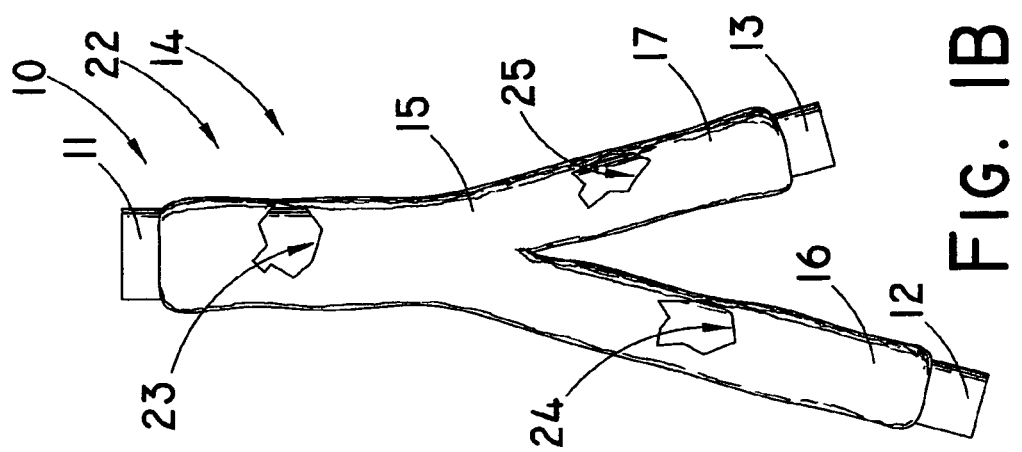
FIG. 1B depicts the mandrel of FIG. 1A with a first layer cast on or applied thereto of a bioremodelable substance such as SIS pieces or particles with or without a binder material.
Figure 1A:
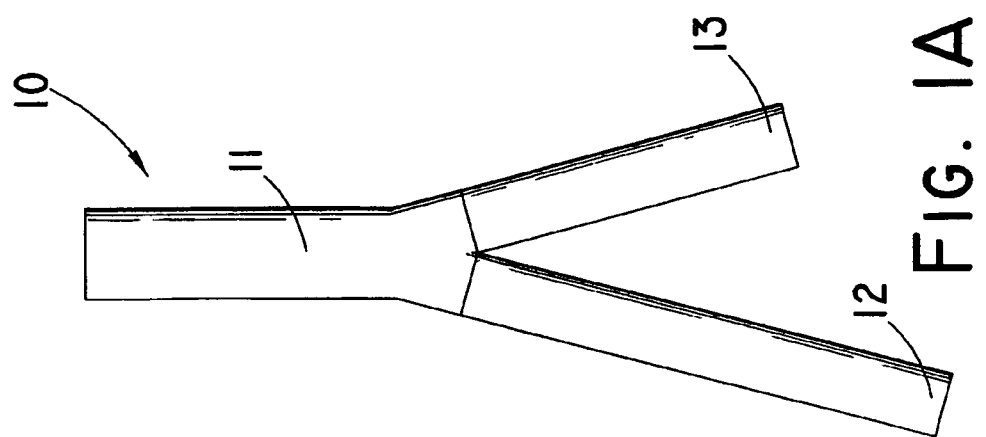
FIG. 1A depicts an illustrative embodiment of a mandrel or form for forming an illustrative bifurcated stent graft of the present invention with a bioremodelable substance such as extracellular collagen matrix (ECM) material and, in particular, small intestine submucosa (SIS) pieces or particles with or without a binder material and having optional expandable members such as Z stents disposed within the substance.

FIG. 1A depicts another illustrative embodiment of a bifurcated form 10 for casting or forming a cast bifurcated bioremodelable graft thereon. In particular, the mandrel or form 10 includes a main body portion 11 and removable ipsilateral and contralateral leg portions 12 and 13 extending from the main body portion. The various portions of the mandrel or form can be made from metal or plastic material tubes or cast from a mold with the appropriate dimensions for accommodating any particular size and shape. Although depicted as a bifurcated mandrel or form, a single elongated member form, preferably having circular cross section, can be used to cast or form the tubular construct graft thereon.

FIG. 1B depicts the mandrel or form 10 of FIG. 1A with a first layer of a liquid or malleable bioremodelable substance 14 cast, applied, or formed thereon. In this illustrative bifurcated embodiment, the bioremodelable substance is cast on or applied to the form to establish a main body portion 15 of bifurcated graft 22 and ipsilateral and contralateral leg portions 16 and 17 extending distally from the main body portion. This first layer of bioremodelable substance can be sprayed on or applied by dipping the form into a liquid form of the bioremodelable substance to establish the first layer on the mandrel. In one particular form of the present invention, this single layer of the bioremodelable substance 14 is allowed to dry or harden to form the bioremodelable graft 22. To reduce the thickness or profile of this single layer graft, the graft can be dehydrated at room temperature to form a rigid tubular construct. The graft can also be frozen and dehydrated in a vacuum chamber to form a lyophilized material construct. Alternatively, the single layer graft can be wrapped with a tightly wound strip of polymer material such as polytetrafluoroethylene or expanded polytetrafluoroethylene and then vacuum pressed to reduce the wall thickness of the graft. This vacuum pressing technique includes placing the tubular construct and form in a vacuum chamber at approximately room temperature and dehydrating the bioremodelable substance. After drying, hardening, or vacuum pressing, bifurcated mandrel or form 10 is removed from the lumen of graft, thus producing graft 22 with main body lumen 23 and ipsilateral and contralateral lumens 24 and 25 as depicted in the partially sectioned portions of the graft.

The bioremodelable substance of the present invention can include a number of different materials or substances that can remodel tissue or cells coming in direct or approximate contact therewith. The bioremodelable substance includes among other things, growth factors that cause the tissue or cells coming in contact therewith to remodel or regenerate. As with the present invention, the cast graft can be surgically positioned in, for example, the aorta of an animal or human patient to replace diseased tissue thereat. Bifurcated graft 22 can be sutured to healthy tissue of the aorta and iliac arteries during, for example, an open surgical procedure. The bioremodelable substance of the graft then remodels the aortic and iliac arteries and is preferably resorbed after the tissue is remodeled.

In accordance with the present invention, the bioremodelable substance preferably includes an resorbable material which is resorbed by the patient during or after the remodeling of the natural tissue or cells coming in contact therewith. In one preferred embodiment, the bioremodelable substance includes an extracellular collagen matrix material and, in particular, a small intestine submucosa (SIS) material. This SIS material is, for example, harvested from a porcine and disinfected for placement in or against the tissue or cells of another material. This SIS material is commercially available from Cook Biotech, West Lafayette, Ind.

Reconstituted or naturally-derived collagenous materials can also be used in the present invention. Such materials that are at least bioresorbable will provide advantage in the present invention, with materials that are bioremodelable and promote cellular invasion and ingrowth providing particular advantage. Bioremodelable materials may be used in this context to promote cellular growth within the lumen of the vessel. This helps to guard against re-establishment of patency of the vessel through biologic processes after the procedure is completed.

Suitable bioremodelable materials can be provided by collagenous extracellular matrix materials (ECMs) possessing biotropic properties. For example, suitable collagenous materials include ECMs such as submucosa, renal capsule membrane, dermal collagen, dura mater, pericardium, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. As prepared and used, the submucosa material and any other ECM used, may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression.

Further, in addition or as an alternative to the inclusion of such native bioactive components, non-native bioactive components such as those synthetically produced by recombinant technology or other methods, may be incorporated into the submucosa tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the occlusion devices include, for example, antibiotics, thrombus-promoting substances such as blood clotting factors, e.g. thrombin, fibrinogen, and the like. These substances may be applied to the device as a premanufactured step, immediately prior to the procedure (e.g. by soaking the material in a solution containing a suitable antibiotic such as cefazolin), or during or after deployment of the occlusion device in the patient.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

Grafts or stent grafts made according to this invention would eventually remodel to the type of tissue with which it is in contact, meanwhile, maintaining patency of the vessel and excluding the aneurysm to prevent rupture. In this particular application, the ECM material would become vessel endothelium such that the diseased portion of the vessel is replaced by healthy vasculature tissue. The remodeled ECM material forms a protective layer of endothelial tissue over the expandable member such as the stents or stiffening wires, originally embedded within the graft materials, such that the blood flowing through the graft portion would not be in contact with a foreign or synthetic material which could cause thrombus or blood flow turbulence. Further, the expandable member, stents or stiffening wires, after fulfilling their original function, continue to provide support and strength to the newly formed endothelium.

Preferably and a best mode embodiment, the bioresorbable material can be a papier mache like layer or coating of pieces of SIS material. The SIS pieces are hydrated and applied to the bifurcated form 10 with the individual pieces coming in direct contact and over lapping each other to form the tubular construct. The pieces can be applied to form a desired thickness. The bioremodelable substance also preferably includes a binder material to better affix or adhere the pieces of the SIS together. The binder material preferably includes a resorbable material and includes, among others, at least one of a biodegradable polymer, a collagen, fibrin, a fibronectin and a polysaccharide. The biodegradable polymer comprises at least one of a polylactic acid, a glycolic acid, a polycaprolactone, a polyurethane-urea, and a polyhydroxyalkanoate. The collagen, among others, comprises at least one of a purified collagen, a non-purified collagen, a cross-linked collagen, and a non-cross-linked collagen. The polysaccharide comprises at least one of a glycogen, a chitosan, and a glucose. This binder material preferably interconnects the extracellular collagen matrix material, and, in particular, the SIS material pieces.

Figure 4:
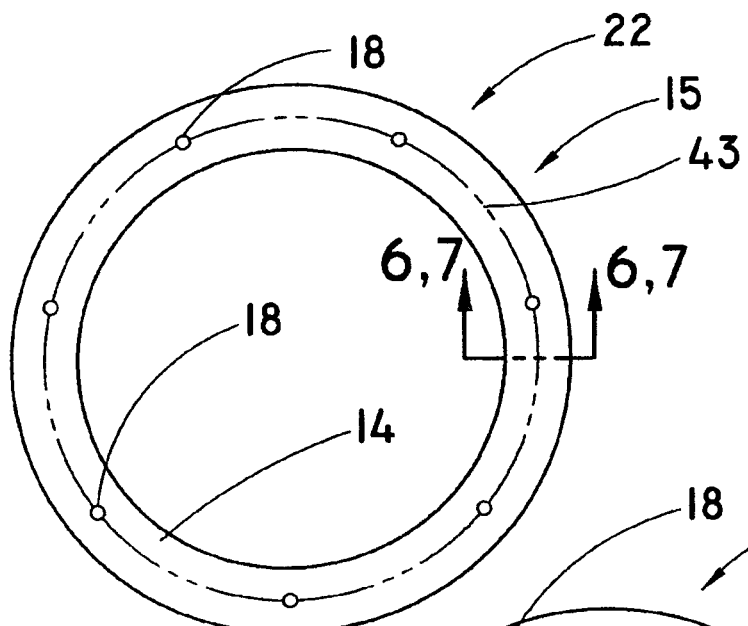
FIG. 4 depicts an end view of the bioremodelable substance wall of the graft of the present invention.
Figure 6:
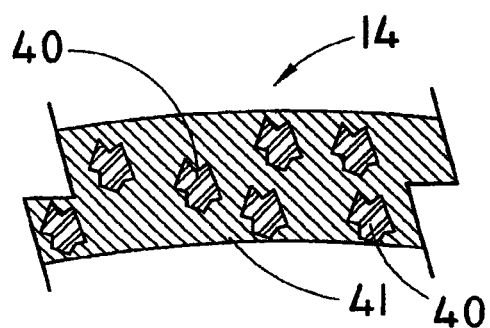
FIG. 6 depicts a partial and enlarged cross-sectional view of the SIS bioremodelable substance layer of the main body portion of the graft of FIG. 4 taken along the line 6-6.

FIG. 4 depicts an end view of main body portion 15 of graft 22 of the present invention of FIG. 1B. FIG. 6 depicts a partial and enlarged cross-sectional view of SIS bioremodelable substance layer 14 of main body portion 15 of graft 22 of FIG. 4 taken along the line 6-6. Layer 14 includes particles of SIS material 40 interconnected by binder material 41.

Figure 7:
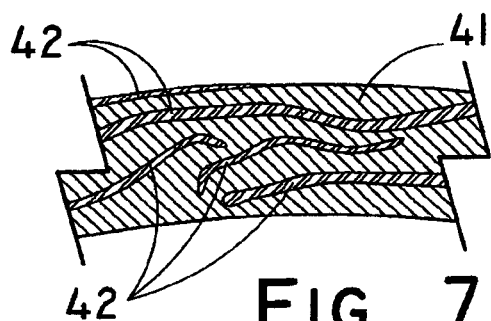
FIG. 7 depicts an enlarged and partially cross-sectional view of the bioremodelable substance layer of the main body portion of the graft of FIG. 4 taken along the line 7-7.

FIG. 7 depicts an enlarged and partially cross-sectional view of bioremodelable substance layer 14 of main body portion 15 of graft 22 of FIG. 4 taken along the line 7-7. In this preferred and best mode embodiment, the layer includes pieces of SIS material 42 that have been hydrated and interconnect one another. In addition, a binder material 41 is utilized to help interconnect the SIS pieces. These pieces can be up to several square centimeters or larger in area and are applied to a mandrel or form much like papier mache. These pieces of SIS material are typically hydrated so as to make them malleable and easily formable on the mandrel or form.

In another embodiment of the present invention, the extracellular collagen matrix material can be ground or formed into small particles or particulate and mixed in with the binder material and then directly applied or cast on form 10. It is also contemplated that other fibers can be mixed in with this bioremodelable substance to provide further strength to the single layer graft. The size, number and concentration of the extracellular collagen matrix material is selected to produce the desired remodeling of tissue or cells coming in contact therewith. Preferably also the binder material is resorbable by the patient after remodeling of the desired tissue has occurred.

FIG. 1C depicts another illustrative embodiment of the present invention of FIG. 1B with one or more expandable members 18 such as well-known and commercially available Gianturco Z stents disposed at least on, in, under or about the first layer of the bioremodelable substance 14. With a single layer of bioremodelable substance, these expandable members or Z stents are applied along the length of the graft and are preferably covered or contained within the single layered graft to expand the stent when, for example, positioned in a patient using a minimally invasive endoluminal surgical technique. However, as depicted, a plurality of expandable member Z stent 18 are positioned longitudinally along the length of the graft in the main body portion 15 as well as leg portions 16 and 17. Each Z stent can be formed from a single piece of wire. A series of Z stents can be laser cut from a cannula tube with interconnecting pieces establishing the longitudinal spacing between the main cylindrical loop segments. As previously indicated, these expandable members can be applied to any bioremodelable substance whether pieces of SIS with or without a binder material or a binder material with particles of extracellular collagen matrix material included therein. The expandable member can also include simply rings or hoops of resilient material such as stainless steel, nitinol or any other resilient material that can expand the bioremodelable graft after release from a compressed state in an endoluminal delivery system.

FIG. 4 depicts an end view of the main body portion 15 of graft 22 of the present invention. The main body portion includes a wall or layer of cast bioremodelable substance 14 with the cross section struts of stent 18. In this particular embodiment, the stents are included in the single layer application of the bioremodelable substance. Alternatively, the stents can be positioned over a first layer of which a second layer of the bioremodelable substance can be applied over the expandable member stents to completely encapsulate the stent in the single layer wall.

Figure 5:
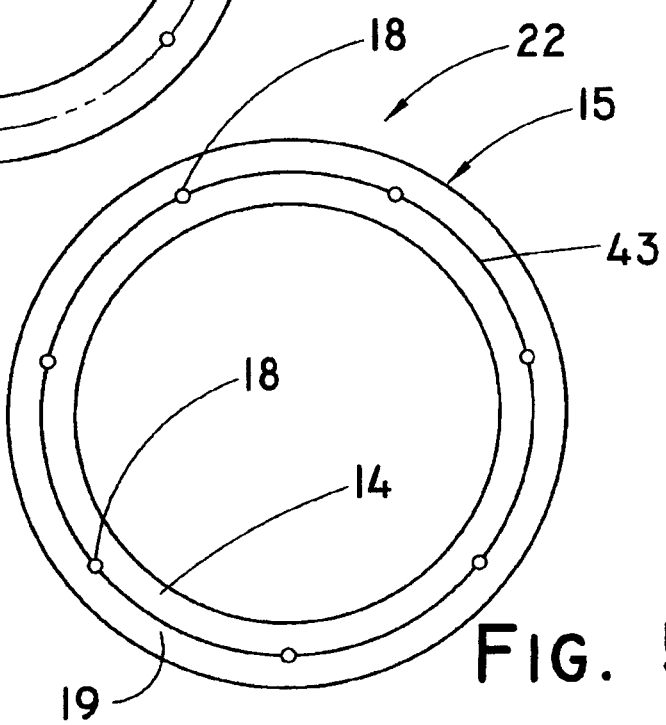
FIG. 5 depicts an alternative embodiment of the end view of the graft of FIG. 4.

FIG. 5 depicts an alternative embodiment of the main body portion 15 of graft 22 in which first layer 14 of bioremodelable substance is applied to the mandrel or form. One or more expandable member stents 18 are disposed on the outer surface of the first layer and then a second layer 19 of the bioremodelable substance is applied thereover. The best mode embodiment of the invention contemplates using two layers of pieces of SIS material with the expandable member stent 18 disposed there between. Depending on the amount of drying or hardening that the first layer experiences, the multilayer construct may appear to be the same as the single layer construct with the interface 43 being difficult to differentiate. This will depend again on the amount of drying or hardening that the layers take on before a second or multiple layers are applied thereto.

FIG. 1D depicts the expandable graft 22 of the present invention of FIG. 1C with a second layer or coating 19 of a bioremodelable substance applied or cast over expandable member stents 18. As a result, the expandable members 18 are cast or contained entirely within one or more layers of the bioremodelable substance. This advantageously eliminates the need for use of sutures or other attachment means for connecting the expandable members to the graft material. As previously indicated, the multiple-layer construct can now be dried, hardened or dehydrated preferably at room temperature. In another way of processing the tubular construct, the multi-layered graft can be frozen and then dehydrated in a vacuum chamber to produce a lyophilized material graft.

FIG. 1E depicts the multi-layer graft 22 of the present invention of FIG. 1D with a strap 28 of polymer such as expandable polytetrafluoroethylene wound tightly around the outer surface of the multi-layer graft still on mandrel or form 10. The winding of strap 28 better controls the thickness of the bioremodelable substance layers to maintain a uniform thickness along the length thereof. After one or more straps 28 are applied along the entire length of the graft, the stent graft is dehydrated and preferably vacuum pressed at room temperature to harden and/or solidify the cast bioremodelable substance layers of the graft.

FIG. 1F depicts multi-layer graft 22 of the present invention of FIG. 1E with form 10 removed from the lumens 23-25 of the graft. This self-expanding multi-layer graft can then be loaded onto a delivery system and compressed to a smaller diameter state using, for example, an outer sheath. The proximal end of the main body portion of the trunk along with the distal end of the ipsilateral and contralateral length portions are trimmed to the desired length prior for placement in the delivery system.

Figure 2:
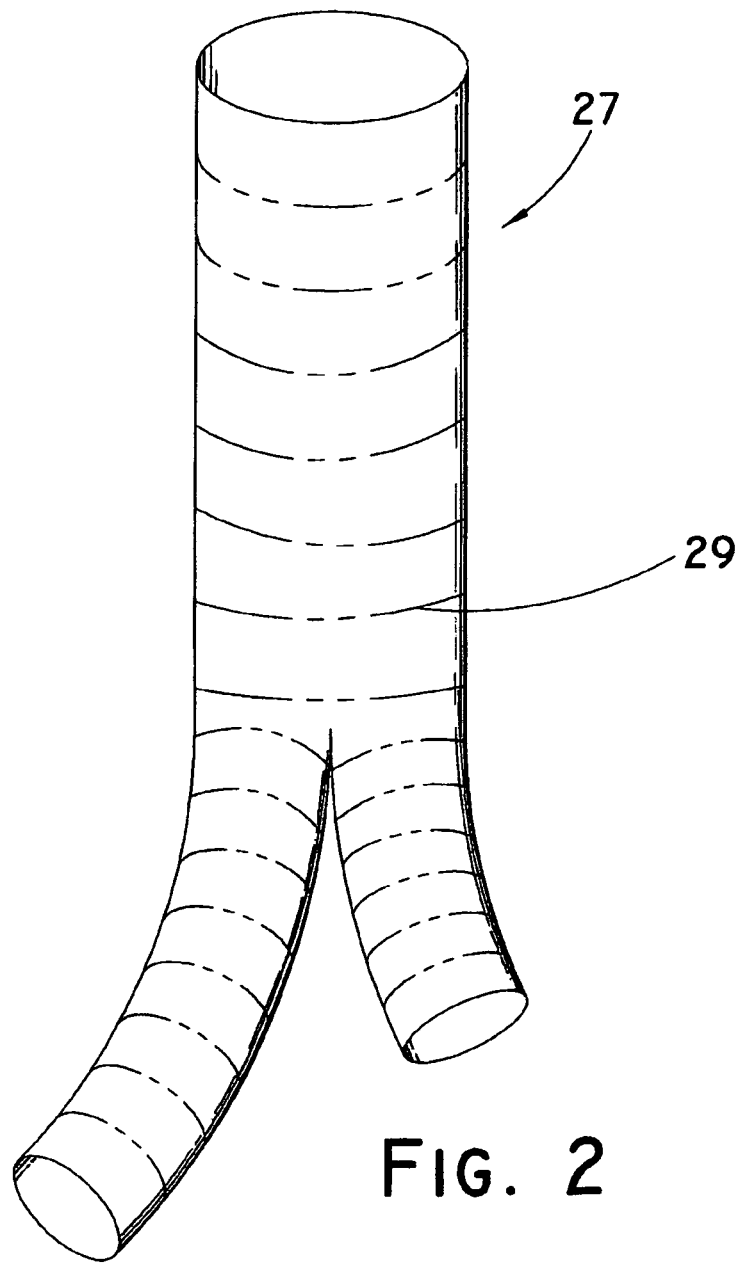
FIG. 2 depicts a woven graft that has nitinol wires or threads incorporated in the weave for support.

FIG. 2 depicts another illustrative embodiment of the present invention of multi-layer graft 27 with, for example, nitinol wire loops 29 positioned longitudinally along the entire length of the graft. Although indicated as a multi-layer bioremodelable graft, the wire loops are expandable members that can be positioned in the bioremodelable substance as it is being cast on or applied to the mandrel or form. This configuration contemplates only a single layer, but the preferred multi-layer graft allows for the more controlled placement and positioning of the expandable members.

Figure 3:
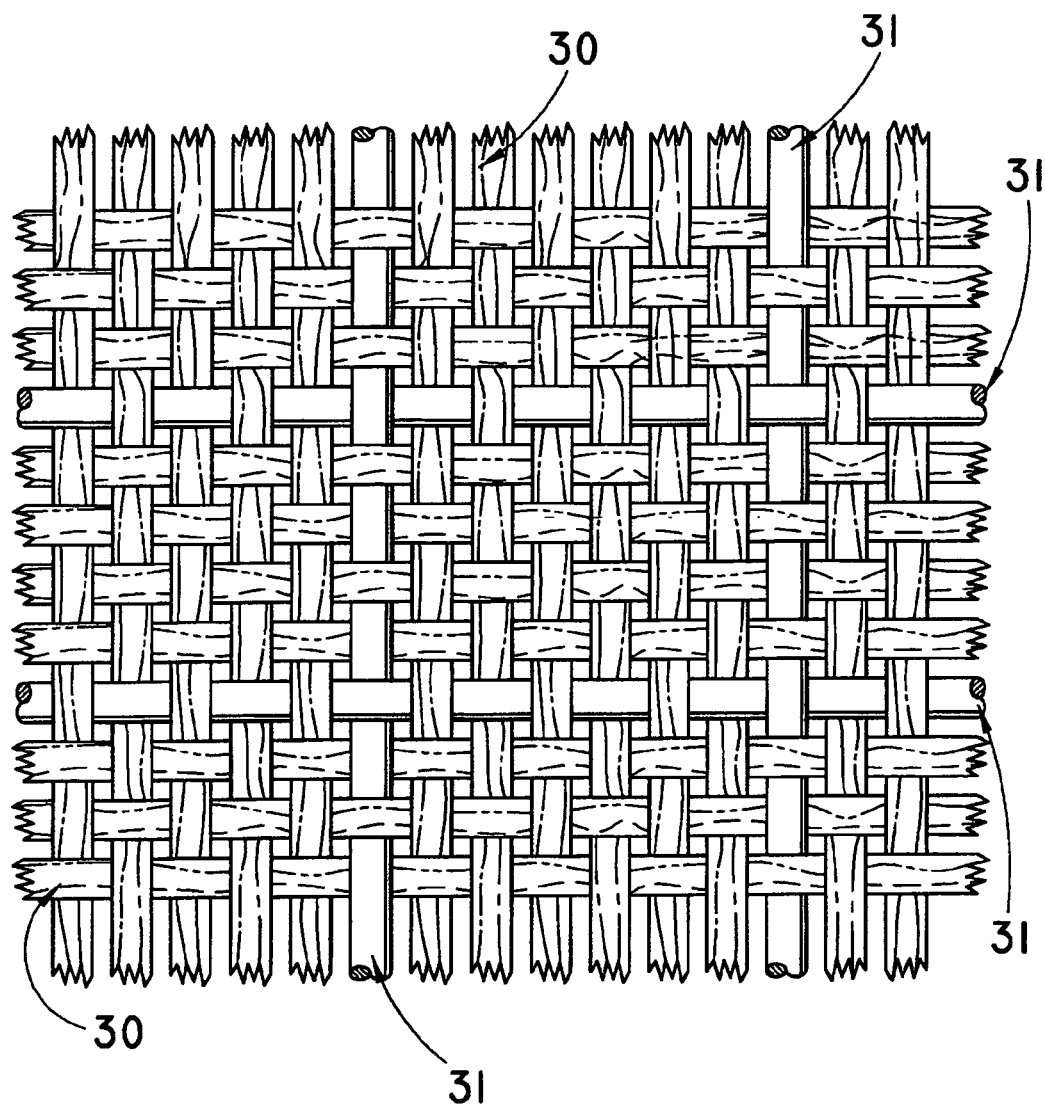
FIG. 3 depicts a magnified view of the weave of the stent in FIG. 2.

FIG. 3 depicts an alternative embodiment of the present invention of a woven bioremodelable graft in which threads 30 of a bioremodelable substance such as, for example, SIS is woven with expandable members such as nitinol, stainless steel or any other resilient material wires 31 that form weft and warf members for circumferential and longitudinal support and self-expansion of the graft. This woven configuration can be used alone for the graft or in combination with a cast tubular construct as previously described.

It is contemplated that numerous materials can be utilized for the bioremodelable substance, included the previously indicated binder material. It is also understood that common dictionary meanings of cast are to be applied in this particular configuration. One such definition of cast is available from the McGraw-Hill Dictionary of Scientific and Technical Terms, $5^{th}$ edition, copyright 1994, page 322, in which cast is defined as to form a liquid or plastic substance into a thick shape by letting it cool in a mold. It is also understood that cast will include any object which is formed by placing a castable substance in a mold or form and allowing it to solidify. In this particular application, cast also contemplates applying a liquid or malleable bioremodelable substance to the surface of the herein described mandrel or form in either a single or bifurcated lumen configuration. Cast also includes applying one or more layers to this mandrel or form or molding the graft within a mold and another form included therein to create the single or multi lumens. It is also contemplated that the bioremodelable substance, with or without a binder material, can include fibers, or another reinforcing materials. The bioremodelable substance can be a gel, a dough, or any other liquid, pliable or malleable substance that can be applied to the herein described mandrel or form and allowed to dry or harden.

Byway of incorporation by reference herein, the following patents are included for a more detailed description of any and all forms of the bioremodelable substance. These references include U.S. Pat. No. 4,902,508, Tissue Graft Composition; U.S. Pat. No. 4,956,178, Tissue Graft Composition; U.S. Pat. No. 5,275,826, Fluidized Intestinal Submucosa and its Use as an Injectable Tissue Graft; U.S. Pat. No. 5,281,422, Graft For Promoting Autogenous Tissue Growth; U.S. Pat. No. 5,352,463, Tissue Graft for Surgical Reconstruction of a Collagenous Meniscus And Method Therefor; U.S. Pat. No. 5,372,821, Graft for Promoting Autogenous Tissue Growth; U.S. Pat. No. 5,445,833, Tendon or Ligament Graft for Promoting Autogenous Tissue Growth; U.S. Pat. No. 5,516,533, Fluidized Intestinal Submucosa and its Use as an Injectable Tissue Graft; U.S. Pat. No. 5,573,784, Graft for Promoting Autogenous Tissue Growth; U.S. Pat. No. 5,641,518, Method of Repairing Bone Tissue; U.S. Pat. No. 5,645,860, Tissue Graft and Method for Urinary Urothelium Reconstruction Replacement; U.S. Pat. No. 5,695,998, Submucosa as a Growth Substrate for Islet Cells; U.S. Pat. No. 5,711,969, Large Area Submucosal Tissue Graft Constructs; U.S. Pat. No. 5,753, 267, Method for Enhancing Functional Properties of Submucosal Tissue Graft Constructs; U.S. Pat. No. 5,755,791, Perforated Submucosal Tissue Graft Constructs; U.S. Pat. No. 5,762,966, Tissue Graft and Method for Urinary Urothelium Reconstruction Replacement; U.S. Pat. No. 5,866,414, Submucosa Gel as a Growth Substrate for Cells; U.S. Pat. No. 5,885,619, Large Area Submucosal Tissue Graft Constructs and Method for Making the Same; U.S. Pat. No. 5,955,110, Multilayered Submucosal Graft Constructs and Method for Making Same; U.S. Pat. No. 5,968,096, Method of Repairing Perforated submucosal Tissue Graft Constructs; U.S. Pat. No. 5,997,575, Perforated Submucosal Tissue Graft Constructs; U.S. Pat. No. 6,087,157, Device and Method of Analyzing Tumor Cell Invasion of an Extracellular Matrix; U.S. Pat. No. 6,096,347, Myocardial Graft Constructs; U.S. Pat. No. 6,126, 686, Artificial Vascular Valves; U.S. Pat. No. 6,187,039, Tubular Submucosal Graft Constructs; U.S. Pat. No. 6,241, 981, Composition and Method for Repairing Neurological Tissue; U.S. Pat. No. 6,264,992, Submucosa as a Growth Substrate for Cells; U.S. Pat. No. 6,331,319, Galactosidase Modified Submucosal Tissue; U.S. Pat. No. 6,375,989, Submucosa Extracts; U.S. Pat. No. 6,206,931, Graft Prosthesis Materials; U.S. Pat. No. 6,358,284, Tubular Grafts from Purified Submucosa; U.S. Pat. No. 5,554,389, Urinary Bladder Submucosa Derived Tissue Graft; U.S. Pat. No. 6,099,567, Stomach Submucosa Derived Tissue Graft. In addition, the indicated US and World Intellectual Property Organization patents or publication numbers and the appropriate issue or publication date is hereby incorporated by reference in their entirety. These additional US and World Intellectual Property Organization publications are as follows: U.S. Pat. No. 6,666, 892, Multi-formed Collagenous Biomaterial Medical Device 2003 Dec. 23; U.S. 20030051735A1, Vessel Closure Member, Delivery Apparatus, and Method of Inserting the Member 2003 Mar. 20; WO 03092546A2, Sling for Supporting Tissue 2003 Nov. 13; WO 03092471A2, Cell-Seeded Extracellular Matrix Grafts 2003 Nov. 13; WO 03088844A1, Apparatus and Method for Producing a Reinforced Surgical Staple Line 2003 Oct. 30; WO 03035125A3, Medical Graft Device with Meshed Structure 2003 May 1; WO 03035125A2, Medical Graft Device with Meshed Structure 2003 May 1; WO 03009764A1, Vessel Closure Member and Delivery Apparatus 2003 Feb. 6; WO 03002168A1, Porous Sponge Matrix Medical Devices and Methods 2003 Jan. 9; WO 03002165A1 Graft Prosthesis Devices Containing Renal Capsule Collagen 2003 Jan. 9; WO 0156500A, Implantable Vascular Device 2001 Aug. 9; WO 0154625A1, Stent Valves and Uses of Same 2001 Aug. 2; WO 0110355A1, Tubular Graft Construct 2001 Feb. 15; WO 0032253A1, Radiopaque Implantable Collagenous Biomaterial Device 2000 Jun. 8; WO 0032250A1, A Multi-formed Collagenous Biomaterial Medical Device 2000 Jun. 8 and WO 0032112A1, Embolization Device 2000 Jun. 8. All of the aforementioned references are incorporated by reference herein and may be referred to for detailed descriptions and support for any of the aforementioned embodiments and descriptions of the cast bioremodelable substance including any binder material. It is also contemplated that the bioremodelable substance can be cross-linked as described in the aforementioned references to control the amount of remodeling of tissue coming in proximity to the bioremodelable substance.

What is claimed is:

1. A cast bioremodelable graft comprising:
an expandable member, and
a cast or molded tubular construct comprising a dehydrated mixture comprising a binder material, and a plurality of cut, shredded or ground pieces of a bioremodelable substance,
wherein the bioremodelable substance is an compressed extracellular collagen matrix material,
wherein the bioremodelable substance is mixed in with the binder material,
wherein the binder material is a resorbable material comprising at least one of a biodegradable polymer, a collagen, a collagen fibrin, a fibronectin and a polysaccharide, wherein the expandable member is embedded within the tubular construct and wherein the graft and the expandable member are free of sutures or other attachment elements connecting the expandable member to the tubular construct.

2. The graft of claim 1, wherein said tubular construct further comprises at least one of a growth factor, and a synthetic material.

3. The graft of claim 1, wherein said extracellular collagen matrix material comprises submucosa.

4. The graft of claim 3, wherein said pieces of extracellular collagen matrix material are vacuum pressed pieces of compressed extracellular collagen matrix material.

5. The graft of claim 1, wherein said expandable member comprises at least one of a resilient material, stainless steel, a shape memory alloy and a superelastic alloy.

6. The graft of claim 1, wherein the tubular construct comprises a first layer and a second layer of a binder material, and a plurality of cut, shredded or ground pieces of extracellular collagen matrix material, wherein the expandable member is embedded between the first layer and the second layer.

7. The graft of claim 1, wherein said binder material is a resorbable material including at least one of a biodegradable polymer comprising at least one of a polylactic acid, a glycolic acid, a polycaprolactone, a polyurethane-urea, and a polyhydroxyalkanoate; a collagen comprising a purified collagen, a non-purified collagen, a cross-linked collagen, and a non-cross-linked collagen; a collagen fibrin; a fibronectin; and a polysaccharide comprising at least one of a glycogen, a chitosan, and a glucose.

8. The graft of claim 1, wherein the tubular construct is a molded tubular construct.

9. The graft of claim 8, wherein the tubular construct is molded onto the expandable member.

10. A cast bioremodelable expandable graft comprising:
an expandable member and a cast or molded tubular construct comprising a dehydrated mixture comprising a plurality of pieces of compressed extracellular matrix material mixed in a biodegradable polymer,
wherein the expandable member is embedded within the tubular construct and wherein the graft and the expandable member are free of sutures or other attachment elements connecting the expandable member to the tubular construct.

11. The expandable graft of claim 10, wherein said tubular construct comprises a first layer of said dehydrated mixture and a second layer of said dehydrated mixture and wherein said expandable member is disposed between said first and said second layers.

12. The expandable graft of claim 10, wherein said tubular construct includes an inner surface and an outer surface and wherein said expandable member is disposed between said inner and said outer surfaces.

13. The expandable graft of claim 10, wherein said tubular construct includes a bifurcated construct having a main body portion having a main body lumen extending therein and first and second leg portions having respective first and second leg lumens extending therein communicating with said main body lumen.

14. A cast bioremodelable graft comprising:
   an expandable member, and
   a cast or molded tubular construct comprising a dehydrated mixture comprising a plurality of overlapping pieces of an extracellular collagen matrix material mixed in a binder material;
   wherein the binder material interconnects the extracellular collagen matrix material,
   wherein the expandable member is embedded within the tubular construct and wherein the graft and the expandable member are free of sutures or other attachment elements connecting the expandable member to the tubular construct.

15. The graft of claim 14, wherein said tubular construct comprises a first layer and a second layer, wherein the expandable member is embedded between the first layer and the second layer.

16. The graft of claim 14, wherein said extracellular collagen matrix material comprises small intestine submucosa material.

17. The graft of claim 16, wherein said binder material is a resorbable material including at least one of a biodegradable polymer comprising at least one of a polylactic acid, a glycolic acid, a polycaprolactone, a polyurethane-urea, and a polyhydroxyalkanoate; a collagen comprising at least one of a purified collagen, a non-purified collagen, a cross-linked collagen, and a non-cross-linked collagen; a collagen fibrin; a fibronectin; and a polysaccharide comprising at least one of a glycogen, a chitosan, and a glucose.

* * * * *

UNITED STATES PATENT AND TRADEMARK OFFICE
CERTIFICATE OF CORRECTION

| | | |
|---|---|---|
| PATENT NO. | : 8,808,352 B2 | Page 1 of 1 |
| APPLICATION NO. | : 11/054043 | |
| DATED | : August 19, 2014 | |
| INVENTOR(S) | : Eells et al. | |

It is certified that error appears in the above-identified patent and that said Letters Patent is hereby corrected as shown below:

On the Title Page:

Left column, item (73), immediately after "Cook Medical Technologies LLC, Bloomington, IN (US)" insert --; Cook Biotech Inc., West Lafayette, IN (US)--.

On the Title Page:

The first or sole Notice should read --

Subject to any disclaimer, the term of this patent is extended or adjusted under 35 U.S.C. 154(b) by 530 days.

Signed and Sealed this
Twenty-second Day of March, 2016

Michelle K. Lee
*Director of the United States Patent and Trademark Office*